United States Patent
Barohn et al.

(10) Patent No.: US 12,128,012 B2
(45) Date of Patent: Oct. 29, 2024

(54) KETAMINE TREATMENT FOR AMYOTROPHIC LATERAL SCLEROSIS

(71) Applicant: University of Kansas, Lawrence, KS (US)

(72) Inventors: Richard Barohn, Kansas City, MO (US); John A. Stanford, Prairie Village, KS (US); Matthew Macaluso, Wichita, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 17/770,543

(22) PCT Filed: May 14, 2021

(86) PCT No.: PCT/US2021/032519
§ 371 (c)(1),
(2) Date: Apr. 20, 2022

(87) PCT Pub. No.: WO2021/231905
PCT Pub. Date: Nov. 18, 2021

(65) Prior Publication Data
US 2023/0066347 A1    Mar. 2, 2023

Related U.S. Application Data

(60) Provisional application No. 63/025,778, filed on May 15, 2020.

(51) Int. Cl.
*A61K 31/135* (2006.01)
*A61P 25/28* (2006.01)

(52) U.S. Cl.
CPC ............ *A61K 31/135* (2013.01); *A61P 25/28* (2018.01)

(58) Field of Classification Search
CPC .............................. A61K 31/135; A61P 25/28
See application file for complete search history.

(56) References Cited

U.S. PATENT DOCUMENTS

| | | |
|---|---|---|
| 2011/0223205 A1 | 9/2011 | Gosiewska et al. |
| 2015/0056308 A1 | 2/2015 | Charney et al. |
| 2018/0094026 A1 | 4/2018 | Moskal |
| 2018/0297928 A1 | 10/2018 | Dugan et al. |

FOREIGN PATENT DOCUMENTS

WO    WO 2016186968    * 11/2016

OTHER PUBLICATIONS

Ketamine Therapy FAQ (Ketamine-Therapy-FAQs.ashx.pdf, Oct. 2016) (hereinafter KTF).*
Roos (Depression in amyotrophic later sclerosis, American Academy of Neurology, 2016, pp. 2271-2277).*
Ohio state (Ketamine Advanced care for Depression at Ohio state, *Ketamine Advanced Treatment for Depression _ Ohio State Medical Center.pdf, Jan. 2020).*
Martinez-Paya (Monitoring Progression of Amyotrophic Lateral Sclerosis Using Ultrasound Morpho-Textural Muscle Biomarkers: A Pilot Study, Ultrasound in Medicine & Biology vol. 44, No. 1, 2018)(hereinafter "Paya").*
United States Patent and Trademark Office; International Search Report and Written Opinion issued in Application No. PCT/US21/32519 dated Aug. 13, 2021; 7 pages.

* cited by examiner

*Primary Examiner* — Kevin E Weddington
(74) *Attorney, Agent, or Firm* — MASCHOFF BRENNAN

(57) ABSTRACT

A method of treating amyotrophic lateral sclerosis (ALS) is provided to extend life expectancy in a subject. The method can include administering the ketamine to a subject having ALS such that the subject has an extended life expectancy compared to life expectancy of the subject prior to being administered the ketamine. The extended life expectancy is determined by the subject having a first progression rate of ALS prior to being administered ketamine and a second progression rate of ALS after being administered ketamine. The first progression rate is faster than the second progression rate such that the progression of ALS in the subject is slowed by the ketamine.

20 Claims, 3 Drawing Sheets

KETAMINE TREATMENT FOR AMYOTROPHIC LATERAL SCLEROSIS

CROSS-REFERENCE TO RELATED APPLICATIONS

This patent application claims priority to U.S. Provisional Application No. 63/025,778 filed May 15, 2020, which provisional is incorporated herein by specific reference in its entirety.

BACKGROUND

Field

The present disclosure relates to ketamine compounds and/or materials containing ketamine compounds for use as a treatment of a subject having Amyotrophic Lateral Sclerosis (ALS).

Description of Related Art

There are currently two FDA-approved drug treatments for Amyotrophic Lateral Sclerosis (ALS): (1) riluzole; and (2) edaravone. Riluzole is believed to attenuate excitotoxicity by blocking sodium channels (Song et al., 1997) and kainate and N-Methyl-D-aspartic acid or N-Methyl-D-aspartate (NMDA) receptors (Debono et al, (1993) Inhibition by riluzole of electrophysiological responses mediated by rat kainate and NMDA receptors expressed in *Xenopus oocytes*. Eur J Pharmacol 235(2-3):283-9). Riluzole also facilitates glutamate uptake (Azbill et al., (2000) Riluzole increases high-affinity glutamate uptake in rat spinal cord synaptosomes. Brain Res 871(2):175-80). Edaravone is thought to provide neuroprotection through its antioxidant and free radical scavenging properties (Watanabe et al., (2018) How is edaravone effective against acute ischemic stroke and amyotrophic lateral sclerosis? J Clin Biochem Nutr 62(1): 20-38). Although these drugs are effective against disease mechanisms in ALS, their effects on disease progression and survival are negligible (Miller et al., (2012) Riluzole for amyotrophic lateral sclerosis (ALS)/motor neuron disease (MND). Cochrane Database Syst Rev. PMID: 22419278; PMCID: PMC7055506; Jaiswal M K. Riluzole and edaravone: A tale of two amyotrophic lateral sclerosis drugs. Med Res Rev. 2019 March; 39(2):733-748. doi: 10.1002/med.21528. Epub 2018 Aug. 12. PMID: 30101496.). Consequently, the search for more effective pharmacotherapeutics for treating ALS and inhibiting the effects of ALS disease progression continues.

Recent studies suggest that ketamine may exhibit neuroprotective properties (Bell, 2017). These properties have been demonstrated in animal models of stroke, traumatic brain injury, and epilepsy (reviewed in Bell, (2017) In Vogue: Ketamine for Neuroprotection in Acute Neurologic Injury. Anesth Analg. 124(4):1237-1243). Although ketamine inhibits NMDA receptor function, its pharmacological properties are complex (Potter & Choudhury, (2014) Ketamine: repurposing and redefining a multifaceted drug. Drug Discov Today. 19(12):1848-54). Unlike riluzole, ketamine likely attenuates NMDA receptor-related glutamate excitotoxicity indirectly. In vitro studies using PC-12 cells reveal that ketamine lowers intracellular D-serine concentrations (Singh et al., (2016) Ketamine Metabolites Enantioselectively Decrease Intracellular D-Serine Concentrations in PC-12 Cells. PLoS One. 11(4):e0149499). D-serine is a co-agonist at the NMDA receptor and contributes to NMDA excitotoxicity. Ketamine also has partial dopamine agonist properties (Kapur & Seeman, (2002) NMDA receptor antagonists ketamine and PCP have direct effects on the dopamine D(2) and serotonin 5-HT(2)receptors-implications for models of schizophrenia. Mol Psychiatry. 837-44; Seeman et al., (2009) Seeman P, Guan H C, Hirbec H (2009) Dopamine D2High receptors stimulated by phencyclidines, lysergic acid diethylamide, salvinorin A, and modafinil. Synapse. 63(8):698-704.), which may also confer neuroprotection (Schapira, (2002) Neuroprotection and dopamine agonists. Neurology. 58(4 Suppl 1):59-18).

SUMMARY

In some embodiments, a method of treating amyotrophic lateral sclerosis (ALS) in a subject is provided. The method can include: providing ketamine and administering the ketamine to a subject having ALS. In some aspects, the ketamine is administered so that the subject has an improvement of a condition of ALS. In some aspects, the improvement in the condition of ALS includes at least one of: improvement in probability of survival; improvement in rate of deterioration of body weight; improvement in projected days of survival; or improvement in days of life after 20% loss of body weight before death.

In some embodiments, the ketamine is administered so that the subject has an extended life expectancy. The extended life expectancy can be determined by a higher probability of survival compared to without being administered ketamine. Also, the extended life expectancy can be determined by a higher probability of survival compared to another subject having ALS with a similar life expectancy that is not administered ketamine.

In some embodiments, the ketamine is administered so that the subject has slower rate of deterioration of body weight. In some aspects, the slower rate is compared to a rate of deterioration of body weight of the subject prior to being administered ketamine.

In some embodiments, the ketamine is administered so that the subject has a higher number of projected days of survival. The higher number of projected days of survival can be compared to a number of projected days of survival for the subject prior to being administered ketamine.

In some embodiments, administering the ketamine after the subject has lost 20% of body weight compared to an initial body weight so that the subject has an improvement in days of life until death. The improvement in days of life can increase latency between 20% loss of body weight and death.

In some embodiments, the subject is diagnosed with ALS and can have symptoms of ALS. In some aspects, the subject being administered ketamine has less than or about 80% body weight compared to an initial body weight. In some aspects, the ketamine is administered in dosing from about 0.1 mg/kg to about 100 mg/kg. In some aspects, the administering is an IV infusion. In some aspects, the dosing is at most every other day. In some aspects, the dosing includes dosing twice weekly for a first period of time and then once weekly for a second period of time.

In some embodiments, a method of treating amyotrophic lateral sclerosis (ALS) to extend life expectancy in a subject can include administering the ketamine to a subject having ALS such that the subject has an extended life expectancy compared to life expectancy of the subject prior to being administered the ketamine. The extended life expectancy is determined by the subject having a first progression rate of ALS prior to being administered ketamine and a second progression rate of ALS after being administered ketamine. The first progression rate is faster than the second progression rate such that the progression of ALS in the subject is slowed by the ketamine.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1:
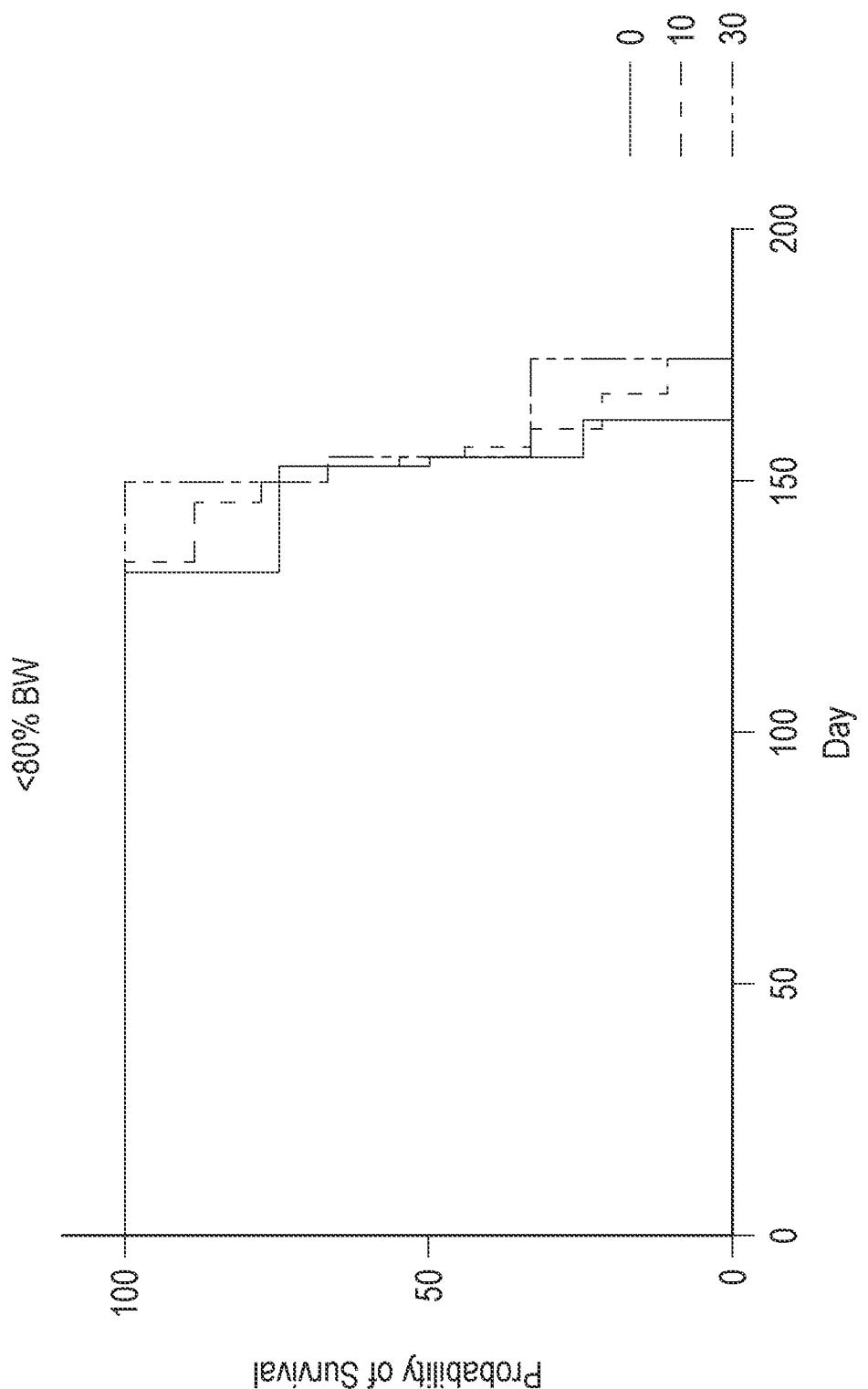
FIG. 1 includes a graph that shows data for ketamine treatment for probability of survival for mice that have lost weight and are at less than 80% initial body weight.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to using ketamine or a derivative thereof (ketamine compound) in pharmaceutical compositions for treating a subject that has Amyotrophic Lateral Sclerosis (ALS). The treatment of ALS with the ketamine compound can be useful in extending the life of the subject so that the subject can have a longer life than expected without the treatment. The ketamine compound can reduce or inhibit progression of ALS symptoms, which then allows the ALS subject to live longer than expected without the treatment. The ketamine compound can be administered to the subject to inhibit disease progression and promote survival of the subject. In part, the promotion of survival can be achieved due to the ketamine compound inhibiting the effects of ALS disease progression as described herein. The data provided herein indicate that ketamine can be administered to ALS patients in order to inhibit progression of symptoms and increase the life expectancy to increase the number of days the ALS patient lives.

The ketamine compound can be administered to the subject in an effective amount to inhibit muscle loss so that the subject retains more muscle for a longer period of time. The inhibition of muscle loss can be in the inhibition of the rate at which muscle is lost in an ALS subject or reducing the amount of the muscle mass that is lost in an ALS subject. The reduction of muscle loss obtained from the ketamine compound may contribute to the subject having an extension of life. That is, the subject can have their life expectancy extended by treatment with ketamine. For example, a subject with ALS may have a life expectancy determined due to the ALS disease progressions that can then be extended to have a longer life expectancy upon treatment with the ketamine compound. The data indicates the decrease in body weight loss can be attributed to less muscle being loss, and thereby ketamine can be administered to inhibit muscle loss.

The ketamine compound can be administered to the subject in an effective amount to inhibit loss of muscle function so that paralysis can be delayed. By inhibiting muscle loss, muscle function is retained with less functionality being lost. The reduction in loss of muscle function obtained from the ketamine compound may contribute to the subject having an extension of life. The data indicates muscle loss can reduce muscle function, and thereby ketamine can be administered to inhibit losing muscle function.

In some embodiments, a method of treating ALS to extend life expectancy in a subject is provided. The method can include providing ketamine, such as in an administrable form. Various administrable forms are described herein. While intravenous administration is described, it should be recognized that oral, transmucosal, transdermal, pulmonary, or other types of injections (e.g., non-IV) could be used. The treatment of ALS is achieved through administering the ketamine to a subject having ALS. The ketamine is administered in an amount and regimen such that the subject has an extended life expectancy. The extended life expectancy is determined based on the standard of life expectancy that the subject has due to ALS prior to receiving the ketamine treatment compared to the prediction that the subject has an expectedly longer life after or during receiving the ketamine treatment. The expectedly longer life is correlated with the data that shows administering the ketamine to the ALS subject (e.g., mouse model) resulted in more days of life left compared to those that did not receive ketamine treatment. In some aspects, the increase in predicted life expectancy can be measured by measuring the amount of mass lost or the rate of mass lost for the subject. This data can be compared to the status of the ALS subject prior to receiving ketamine. The method can be performed with a subject that has been diagnosed with ALS. In most instances, the subject is in a symptomatic stage of ALS. However, the method may also be performed when the subject is in a pre-symptomatic stage of ALS based on the evidence that ketamine improves the outcome of ALS patients. The data indicates the decrease in body weight loss can be correlated to a better life expectancy, such as shown by the latency of 20% body weight loss until death being extended with ketamine, and thereby ketamine can be administered to increase the probability of survival and thereby increase life expectancy.

The protocol for administering the ketamine in a treatment regimen in the subject can be performed sufficiently to slow deterioration of neuromuscular strength in the subject. The deterioration of neuromuscular strength in the subject can be determined before (e.g., control) or after administering the ketamine treatment regimen. The data of the treated subject can then be compared to neuromuscular strength deterioration of the subject prior to being administered the ketamine. Also, the data of the treated subject can be compared to a defined standard of neuromuscular strength. Additionally, the data of the treated subject can be compared to average neuromuscular strength across a population of a plurality of subjects, such as subjects with ALS as well as subjects at a similar ALS disease state (e.g., similar symptoms or muscle function).

The protocol for administering the ketamine in a treatment regimen in the subject can be performed sufficiently to slow deterioration of mass in the subject. The deterioration of mass in the subject can be determined before and after administering the ketamine treatment regimen. The data of the treated subject can then be compared to mass deterioration of the subject prior to being administered the ketamine. Also, the data of the treated subject can be compared to a defined standard of mass deterioration, such as at a corresponding disease state or ALS progression. Additionally, the data of the treated subject can be compared to average mass deterioration across a population of a plurality of subjects, such as subjects with ALS as well as subjects at a similar ALS disease state (e.g., similar symptom, mass loss).

In some embodiments, administering the ketamine to the subject is provided in a treatment regimen that slows deterioration of neuromuscular strength in the subject compared to neuromuscular strength of other subjects that are not administered the ketamine. The other subjects can be those having ALS (e.g., showing symptoms) or at a pre-symptomatic stage of ALS.

In some embodiments, administering the ketamine to the subject is in a treatment regimen that slows deterioration of mass in the subject compared to mass of other subjects that are not administered the ketamine. The other subjects can be those having ALS (e.g., showing symptoms) or at a pre-symptomatic stage of ALS.

In some embodiments, the treatment can be initiated prior to onset of limb paralysis. This can include administering the ketamine in a treatment regimen that inhibits onset of limb paralysis in the subject. That is, the ketamine is administered before observable limb paralysis. The inhibition of onset of limb paralysis can be monitored by observing limb functionality. The inhibited onset of limb paralysis can be compared to limb paralysis of the subject prior to being administered the ketamine, where inhibition shows no change to minimal change with regard to onset of paralysis. The data indicates muscle loss can result in limb paralysis, and thereby ketamine can be administered to inhibit losing muscle and thereby inhibiting limb paralysis (e.g., loss of limb function).

In some embodiments, the treatment can be initiated after the onset of limb paralysis. This can include administering the ketamine in a treatment regimen that inhibits progression of limb paralysis (e.g., rate of progression) in the subject compared to limb paralysis of the subject prior to being administered the ketamine. That is, the ketamine is administered after observable limb paralysis. The inhibition of progression of limb paralysis can be monitored by observing limb functionality during or after the ketamine treatment. The inhibited progression of limb paralysis can be compared to a state of limb paralysis of the subject prior to being administered the ketamine, where inhibition shows no change to minimal change with regard to progression of paralysis.

In some embodiments, the treatment can be initiated so that the subject can live longer, which is tied to an increase in life expectancy. Prior to the treatment, the subject is identified as having a certain amount of time left in their life before they are expected to die from ALS. During and after the treatment, the ketamine helps the subject so that they are expected to live longer, and thereby have an increase in life expectancy. The treatment to improve life expectancy can include administering the ketamine in a treatment regimen in an amount sufficient such that the ketamine improves the life expectancy in the subject. This improvement in life expectancy in the subject is compared to the life expectancy of the subject identified prior to being administered the ketamine.

For example, the subject is determined to have a decreasing life expectancy such that their life expectancy is decreasing at a first rate prior to being administered ketamine. Then, the subject has a second rate of decreasing life expectancy after being administered a treatment regimen of ketamine. The ketamine treatment results in the first rate being faster than the second rate so that the subject is expected to live longer.

In another example, the subject is determined to have a short life expectancy such that their life expectancy is defined as a term of X length, where the life expectancy of X indicates a shortened life prior to being administered ketamine. Then, the subject has a longer life expectancy after being administered a treatment regimen of ketamine. The longer life expectancy can be greater than X (e.g., X+$\Delta$), where $\Delta$ is the increase in time that the subject is expected to be alive or actually lives. The ketamine treatment results in the subject having a longer life expectancy. For example, the short life expectancy can be 130 days and the longer life expectancy (e.g., probability of survival) can be 150 days. However, it should be recognized that any increase in life expectancy is desirable and beneficial to the subject, even just a single day. Therefore, a measurable increase in the probability of survival can be important, which can be obtained with the ketamine treatment. The ketamine can be administered to the ALS patient in an attempt to increase the length of life left.

In some embodiments, the ketamine can be used in a treatment to improve the disease state or symptom state of the subject over other subjects that are not administered ketamine. The treatment can include administering the ketamine in a treatment regimen that improves life expectancy in the subject compared to a static or decreasing life expectancy of other subjects that are not administered the ketamine. Also, the improvement in life expectancy can be in the greater life term (e.g., X+$\Delta$) achieved with the ketamine treatment. The other subjects can have a symptomatic stage of ALS.

In some embodiments, the treatment includes administering the ketamine in a treatment regimen that improves life expectancy in the subject compared to life expectancy of other subjects that are not administered the ketamine. Here, the subject has a decreasing life expectancy at a first rate after being administered ketamine and the other subjects have a decreasing life expectancy at a second rate and are not administered ketamine. The first rate is slower than the second rate so that the subject has an increase in life expectancy compared to the other subjects.

In some embodiments, the treatment can include administering the ketamine in a treatment regimen that inhibits onset of muscle mass loss in the subject compared to muscle mass loss of the subject prior to being administered the ketamine. In some instance, the subject has not yet had an onset of muscle loss, and thereby the muscle mass loss at a first rate is zero prior to being administered ketamine. In this instance, the ketamine is administered to inhibit the onset of muscle loss in a prophylactic treatment in an attempt to slow progression of ALS. The inhibition of the onset can be a predicted delay in the onset of the muscle loss, whether or not it occurs. However, it should be considered that ALS once diagnosed is likely to have some onset of disease state or symptoms at some point. The diagnosis of ALS indicates that onset of symptoms, such as muscle loss, will occur at some point in the future if it has not yet occurred in the subject. The prophylactic treatment to the subject prior to onset of symptoms can be administered based on the evidence that treatment in symptomatic ALS patients with ketamine inhibits muscle loss, and thereby administration to any ALS patient may be beneficial for inhibiting muscle loss. Any inhibition of onset of muscle loss is important to the ALS patient because it is the retention of muscle that likely allows for an increase in survival.

This includes using any means necessary to inhibit onset of ALS symptoms, such as muscle loss. Due to the ketamine treatment, the onset of muscle wasting can be slowed and the timeline of muscle retention can be increased. As such, the subject that is retaining muscle mass can be administered ketamine to inhibit onset of muscle loss. The inhibition can be any measurable change in the prolonging of muscle retention once ketamine is administered.

In some embodiments, the treatment can include administering the ketamine in a treatment regimen that inhibits progression of muscle mass loss in the subject compared to muscle mass loss of the subject prior to being administered the ketamine. In some instance, the subject has a progression of muscle mass loss at a first rate prior to being administered ketamine and then at a second rate after being administered a treatment regimen of ketamine. Due to the ketamine treatment, the first rate of progression is faster than the second rate of progression. As such, the subject that is losing muscle mass can be administered ketamine to inhibit progression of muscle loss. The inhibition can be any measurable change in prolonging muscle retention once ketamine is administered, which can apply to anything inhibited by the administration of ketamine.

In some embodiments, the treatment can include administering the ketamine in a treatment regimen that inhibits rate of muscle mass loss in the subject compared to rate of muscle mass loss of the subject prior to being administered the ketamine. In some aspects, the subject has a progression of muscle mass loss at a first rate prior to being administered ketamine. Then, the subject has a progression of muscle loss at a second rate after being administered a treatment regimen of ketamine, which is slower muscle loss. This indicates the first rate of muscle loss is faster than the second rate muscle loss achieved with the ketamine treatment. In some aspects, the ketamine treatment regimen inhibits onset or progression or rate of muscle mass loss in the subject compared to progression of muscle mass loss of other subjects that are not administered the ketamine, where the other subjects have a symptomatic stage of ALS.

In some embodiments, the treatment can include administering the ketamine in a treatment regimen that inhibits onset or progression of limb paralysis in the subject compared to limb paralysis of the subject prior to being administered the ketamine. Similar to other treatments, the inhibition can be compared to subjects in a similar ALS disease state that are not administered ketamine. The muscle wasting can lead to limb paralysis, and vice versa. Therefore, inhibiting onset or progression of limb paralysis can lead to the other improvements in quality of life and/or life expectancy extension as described herein.

The ketamine treatment can be used in ALS patients that are symptomatic and experiencing muscle wasting. Accordingly, the ketamine treatment can be administered in an effective amount in an attempt to delay death of the subject. That is, the treatment with ketamine increases the chance of survival for the subject, based on measurable muscle retention/loss data and/or functionality data. Accordingly, the ketamine treatment can be administered in an effective amount to extend survival of the subject, based on measurable muscle retention/loss data. In some aspects, the ketamine treatment is administered in an effective amount to increase latency between initial body mass of subject and loss of 20% of body mass of the subject. In some aspects, the ketamine treatment is administered in an effective amount to delay loss of muscle loss so that it takes longer to lose 20% body mass from an initial body mass (e.g., a body mass prior to contracting ALS or prior to being diagnosed, or at the time of diagnosis). In some aspects, the ketamine treatment is administered in an effective amount to slow a rate of loss of body mass from an initial rate of loss of body mass (e.g., a body mass loss rate prior to contracting ALS or prior to being diagnosed, or at the time of diagnosis). In some aspects, the ketamine treatment is administered in an effective amount to increase a number of days of life that are left for the subject (e.g., increase the number of days until predicted death date). In some aspects, the ketamine treatment is administered in an effective amount to increase quality of life of the subject or at least in an attempt to provide a slowing of the loss of quality of life as ALS progresses. In some aspects, the ketamine treatment is administered in an effective amount to extend survival (e.g., extend probability of survival) of the subject after the subject has muscle wasting. In some aspects, the ketamine treatment is administered in an effective amount to inhibit limb paralysis of the subject, such as hind limb paralysis.

In some embodiments, the ketamine compound is ketamine or a pharmaceutically acceptable salt of ketamine. The structure of ketamine is shown below.

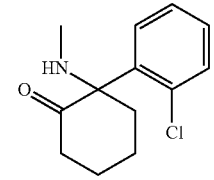 [SMILES: CNC1(c2ccccc2Cl)CCCCC1=O]

Ketamine (2-(2-chlorophenyl)-2-(methylamino)cyclohexan-1-one)

Stereoisomers of compounds (also known as optical isomers) include all chiral, diastereomeric, and racemic forms of a structure, unless the specific stereochemistry is expressly indicated. Thus, ketamine compounds include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

In some embodiments, the ketamine is S-ketamine or a pharmaceutically acceptable salt of S-ketamine. The structure of S-ketamine (aka "esketamine") is shown below.

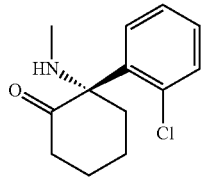 [SMILES: CN[C@]1(c2ccccc2Cl)CCCCC1=O]

S-Ketamine ((S)-2-(2-chlorophenyl)-2-(methyl-amino)cyclohexan-1-one)

In some embodiments, the ketamine is R-ketamine or a pharmaceutically acceptable salt of R-ketamine. The structure of R-ketamine (aka "arketamine") is shown below.

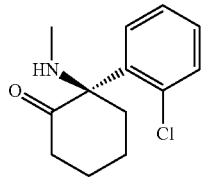 [SMILES: CN[C@@]1(c2ccccc2Cl)CCCCC1=O]

R-Ketamine (R)-2-(2-chlorophenyl)-2-(methyl-amino)cyclohexan-1-one

In a related aspect, a pharmaceutical composition is provided. The pharmaceutical composition can include an effective amount of the ketamine compound of any embodiments of compounds of ketamine or derivatives or pharmaceutically acceptable salt thereof for treating a condition, and where the condition is ALS and associated disease state and state of symptoms. The derivatives can include replacing the Cl with I, Br, or F, or replacing the methyl from the amine with another alkyl, such as $C_2$-$C_{12}$ alkyl.

Pharmaceutically acceptable salts of ketamine are within the scope of the present technology and include acid or base addition salts which retain the desired pharmacological activity and is not biologically undesirable (e.g., the salt is not unduly toxic, allergenic, or irritating, and is bioavailable). When the ketamine has a basic group, such as, for example, an amine group, pharmaceutically acceptable salts can be formed with inorganic acids (e.g., hydrochloric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid).

When the compound of the present technology has an electronegative group, such as for example, a chlorine group, it can form salts with metals, such as alkali and earth alkali metals (e.g. $Na^+$, $Li^+$, $K+$, $Ca^{2+}$, $Mg^{2+}$, $Zn^{2+}$)ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the ketamine compounds having one or more of the utilities described herein, as well as mixtures of these various different forms. "Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. Here, the keto group can form an —OH in a tautomeric form.

As used herein, the term "effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of ALS. As used herein, a "subject" or "patient" is a mammal, such as a cat, dog, rodent or primate. Typically the subject is a human, and, preferably, a human suffering from or suspected of suffering from ALS. The term "subject" and "patient" can be used interchangeably.

Thus, the instant present technology provides pharmaceutical compositions and medicaments comprising any of the ketamines, or derivative thereof, prodrug thereof, salt thereof, or stereoisomer thereof, or having any chirality at any chiral center, or tautomer, polymorph, solvate, or combination thereof as disclosed herein and optionally a pharmaceutically acceptable carrier or one or more excipients or fillers. The compositions may be used in the methods and treatments described herein. Such compositions and medicaments include a therapeutically effective amount of any compound as described herein. The pharmaceutical composition may be packaged in unit dosage form. The unit dosage form is effective in treating ALS when administered to a subject in need thereof.

The pharmaceutical compositions and medicaments may be prepared by mixing one or more compounds of the present technology with pharmaceutically acceptable carriers, excipients, binders, diluents or the like to treat ALS. The compounds and compositions described herein may be used to prepare formulations and medicaments that prevent or treat a variety of symptoms associated with ALS. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via an implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount, such as by simply administering a compound of the present technology to a patient in increasing amounts until the progression of the condition/disease state is decreased or stopped. The ketamine compound can be administered to a patient at dosage levels in the range of about 0.1 to about 100 mg per day or per dose or per kg. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially or synergistically be effective for the treatment of ALS.

In one aspect, a ketamine compound is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from 0.1 mg/kg to about 1 mg/kg, or about 0.25 mg/kg to about 0.75 mg/kg, or about 0.5 mg/kg. However, it should be recognized that the 1 mg/kg is a small dose, and higher dosages are envisioned as described herein. While the data provided herein include higher dosages for mice, data from depression patients show these small dosages may be better tolerated by a human patient.

In some embodiments, the mechanism of ketamine in treating ALS may or may not involve modulation of the glutamate or AMPA receptors. The degree of target modulation necessary to treat ALS in humans may be similar or different than what is necessary in animal models, and may differ from the previous work done in depressed humans with ketamine, all of which may require different degrees of target engagement. Thus, the dosage for the treatment described herein may be modified for use in humans.

Accordingly, ketamine can be administered alone or in combination with riluzole to slow disease progression and improve survival of an ALS patient. In some embodiments, the dosing can include administering ketamine in combination with riluzole for a combination therapy in ALS patients. It may be possible that the combination of ketamine's broad pharmacological profile with that of riluzole may have salutary effects in this model. The combination of ketamine and riluzole can be used as a treatment combination since ALS patients. It is possible that the combination of the two drugs will be more effective than ketamine alone.

In some embodiments, the dosing can include administering ketamine at (e.g., saline vehicle) at up to 10 mg/kg or up to 30 mg/kg can be performed as per the data provided herein. However, while high dosages may be usable, the benefits may arise from low dosages, such as those described herein (e.g., 0.5-1 mg/kg). The dosage can be as little as one time a week; however, twice a week infusion dosing is preferred. The dosing can be up to three times a week or four times a week, but should be at most every other day with a day of no dosage in between. The dosing regime can be from one week to as many weeks as needed or desired by the patient or until the patient dies. The dosing regimen can be tailored for each patient. For example, a patient may be prescribed a regimen that includes dosing twice weekly for four weeks, followed by once weekly for four weeks, then once every other week for four weeks, and then monthly until dosing is stopped or adjusted further at the discretion of the doctor. Dosing should occur no more frequently than every other day. In other words, no two doses should be separated by fewer than 48 hours. The intravenous infusion can be over time (e.g., at least a minute) and not a bolus.

Experiments were conducted with ketamine in ALS patients as described herein. The resulting data strongly suggests that ketamine treatment can improve survival in ALS. They also suggest that ketamine may extend survival once body weight loss from muscle wasting has become marked. It is thought that the optimal dose may be different in humans than SOD1-G93A mice.

In some embodiments, the dosing may be as follows in the tables based on information from treating depression subjects with ketamine. However, based on the data provided herein the dosing may be increased by a factor of 5 to a factor of 10.

High Dosing

| | |
|---|---|
| 7.5 to 12.5 mg/kg | Intramuscular (IM) injection |
| 6.0 to 25.0 mg/kg | Insufflation (intranasal or "inhaling")—pulmonary delivery |
| 5.0 to 10.0 mg/kg | Intravenously (IV) |
| 20.0 to 30.0 mg/kg | Orally (by mouth) |

Midrange Dosing

| | |
|---|---|
| 3.5 to 7.5 mg/kg | Intramuscular (IM) injection |
| 3.5 to 7.5 mg/kg | Insufflation (intranasal or "inhaling")—pulmonary delivery |

-continued

| 3.5 to 7.5 mg/kg | Intravenously (IV) |
| 10.0 to 20.0 mg/kg | Orally (by mouth) |

Low Dosing

| 0.55 to 3.5 mg/kg | Intramuscular (IM) injection |
| 0.5 to 3.5 mg/kg | Insufflation (intranasal or "inhaling")—pulmonary delivery |
| 0.5 to 3.5 mg/kg | Intravenously (IV) |
| 5.0 to 10.0 mg/kg | Orally (by mouth) |

In some embodiments, the dosage is high, such as 10 times the values shown in the above dosing schedule.

An example of a dosage form can include an injectable solution: Schedule III: 0.5 mg/mL; 1.0 mg/mL; 5.0 mg/mL; 10.0 mg/mL; 20.0 mg/mL; 30 mg/mL; 50 mg/mL; or 100 mg/mL.

In some embodiments, ketamine can be administered twice a week to slow disease progression of ALS. This dosing regime can be used to increase survival in subjects, as shown in SOD1-G93A mice.

In some embodiments, the ketamine can be delivered similarly as with treatment of depression, which may be intravenous or intranasal administration.

EXAMPLES

Testing can be performed in SOD1-G93A mice as follows. Body weight and grip strength during a hanging wire test can be measured 3 days a week beginning at 90 days of age (presymptomatic). Drug injections can be made immediately after motor testing. Mice can be tested until they reach end-stage as defined by loss of righting reflex for 30 seconds or if they are found dead in their cage. At death, the muscles (soleus, tibialis anterior, and diaphragm) and brains can be harvested for histological analyses. Comparisons of neuromuscular junction innervation and myosin heavy chain isoforms can be made between the treatment groups. Experiments can determine cortical motor neuronal integrity using standard histological methods.

Experiments were performed to determine the effects of daily sub-anesthetic doses (e.g., less than 100 mg/kg) of ketamine on the SOD1-G93A mouse model of ALS. The method included administering two doses of ketamine (e.g., 10 mg/kg and 30 mg/kg) and a saline vehicle to three groups of SOD1-G93A mice per day for 5 days per week beginning at 90 days of age. The method included measuring body weight, grip strength, and survival.

The data indicated that there were no significant effects of ketamine on body weight or grip strength using the hanging wire test (data not shown). Similar to the overall body weight measures, the survival analysis revealed no significant difference between the groups in the day in which body weight fell below 80% (FIG. 1).

FIG. 1 shows the survival curve for body weight loss as a function of ketamine dose. The three groups (e.g., 12 mice per group with intraperitoneal injection): vehicle (e.g., 0), 10 mg/kg (e.g., 10), and 30 mg/kg (e.g., 30) are shown (p=0.06). As shown, the data for 10 mg/kg shows an improvement in the probability of survival for the groups in the day which the body weight fell below 80%, where this dosage shows an improvement over almost all of the vehicle data. As such, the 10 mg/kg dosage may be useful for ALS patients. Additionally, the trend in the data appears to indicate that the higher dose of 30 mg/kg of ketamine delays loss of body weight (muscle mass) for a longer period of time than the 10 mg/kg ketamine or without ketamine. Accordingly, increasing the amount of ketamine administered may increase the effects described herein. Any increase in life (e.g., probability of survival) can be beneficial, which may be accomplished by treatment with the ketamine compound.

Figure 2:
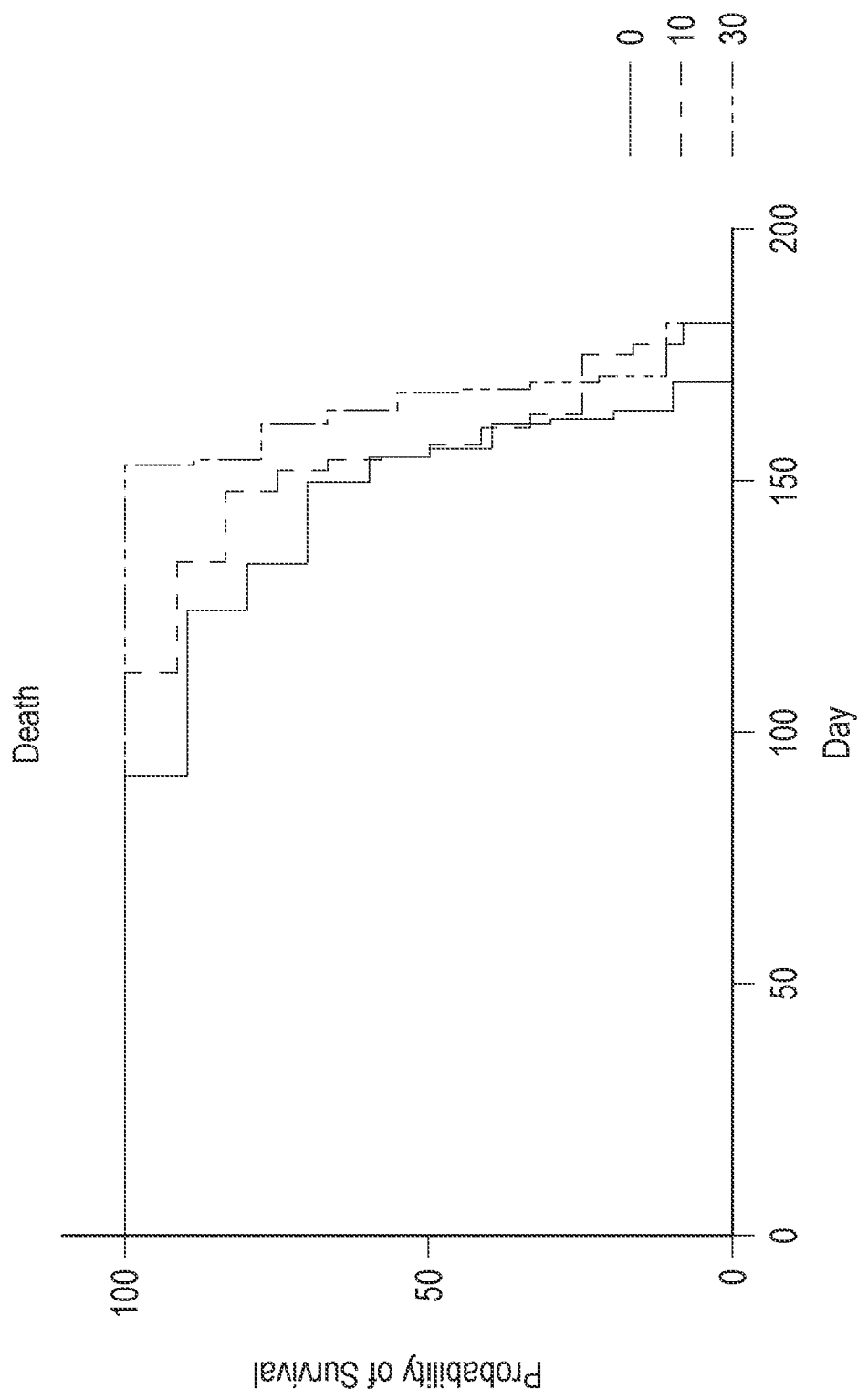
FIG. 2 includes a graph that shows data for ketamine treatment for probability of survival for mice.

Additionally, FIG. 2 shows another survival curve that was created for day of death, defined as a loss of righting reflex for 30 seconds due to paralysis or the mouse being found dead in the cage. As shown, treatment with the ketamine compound appears to provide a higher probability of survival for a longer period of time for both the 10 mg/kg and 30 mg/kg dosages (p=0.06; FIG. 2). While the 10 mg/kg group (e.g., 10) showed some improvement over the vehicle (e.g., 0), the 30 mg/kg group (e.g., 30) had a longer 100% probability of survival and then survived significantly longer than the vehicle-treated group ($p<0.05$) Thus, the data indicates that the effects of ketamine on increasing survival and prolonging life of a subject having ALS are therefore promising. This indicates that it may be possible that higher ketamine dosages can provide still better survival probability. This translates into a longer life expectancy and provides support for the recited embodiments.

Figure 3:
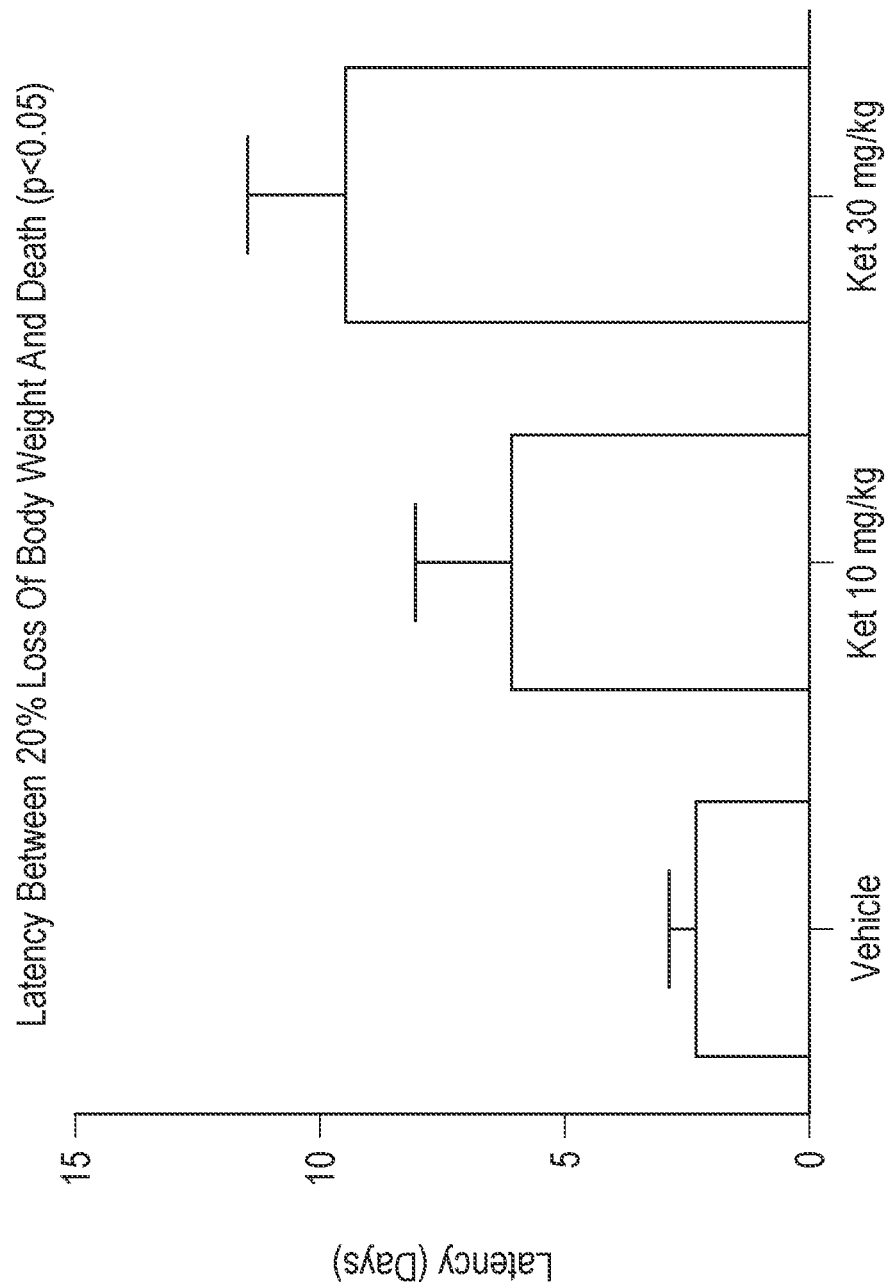
FIG. 3 includes a graph that shows data for ketamine treatment for latency from date mice are at less than 80% initial body weight to date of death.

Additionally, the latency in days between the day in which each mouse reached 80% of its initial body weight (i.e., 20% reduction) and the day of death as defined above was calculated. Ketamine produced a statistically significant dose-dependent increase in the latency between body weight loss and death as shown in FIG. 3. FIG. 3 shows the latency between 20% loss of body weight and death as a function of ketamine dose. The ANOVA revealed a statistically significant effect for dose on the latency measure ($p<0.05$). The vehicle only (no ketamine) only had a latency of life at about 2 days. The 10 mg/kg ketamine showed about 6 days of latency of life, translating to about 4 days of longer life expectancy. The 30 mg/kg showed about 10 days of latency of life, translating to about 8 days longer life expectancy than no treatment, and about 4 days of longer life expectancy over the 10 mg/kg treatment. Accordingly, higher dosages may still provide for longer latency of life, or longer life expectancy.

In some embodiments, the data can be interpreted to indicate that ketamine dosage can extend the latency of days between the day that the body weight declines past a certain percentage of its initial body weight (e.g., 80%) and the day of death. The latency is the increase in days of life obtained from the ketamine treatment. The data indicates the ketamine treatment may extend survival in ALS patients once body weight loss from muscle wasting has become marked, identifiable, or obvious. This can provide for longer survival or a longer life expectancy for ketamine patients compared to others that do not receive the ketamine treatment or for subjects compared to themselves had they not had the ketamine treatment.

The ketamine compound can be studied for safety in order to establish that it can be administered to ALS patients. For example, the trial can be an open label trial of 24 patients with randomized controlled cross over trials with 12 patients receiving ketamine and 12 placebo injections twice a week for a month. Then, the groups of patients switch to the opposite treatment arm, such as those that received the ketamine now receive the placebo and those that received the placebo now receive ketamine. The dose will be sub-anesthetic ketamine infusions: a total of 0.5 mg/kg intravenous infusion over 40 minutes. The patients are monitored throughout for any adverse reactions.

Once determined safe for ALS patients, the efficacy can be studied with same dose and the same criteria for ALS. In addition, the patients can be those that demonstrate a decline of ALS Functional Rating Scale (FRS) of at least 1 point over three months leading into the trial to show they have a progressing ALS disease state. The trial can randomize 120 patients into two arms: (1) ketamine versus (2) placebo infusions. Subjects can receive two infusions of the defined dosage each week for six months. The primary measure of efficacy can be ALS FRS. The study can be performed to show an expected up to 30 percent reduction in the decline of the slope of the ALS FRS over six months. This can be used to show the ketamine compound is effective for ALS in humans, which is expected based on the mouse data provided herein. Patients in this trial can be on Rilutek (riluzole) oral medication but not on Radicava infusions.

Once the ketamine compound is approved by a regulatory agency (e.g., FDA) for use in ALS for the treatments described herein, the ketamine can be administered in an intravenous (IV) infusion. The ketamine infusion can be performed at a medical suite (e.g., physician medical office) twice a week for as long as the patient is alive or until the patient decides to terminate treatment. The ketamine infusion can be from about 0.1 mg/kg to about 1 mg/kg, or about 0.25 mg/kg to about 0.75 mg/kg, or about 0.5 mg/kg.

In some embodiments, dosing of ketamine can occur twice weekly for four weeks, followed by once weekly for four weeks, then once every other week for four weeks, and then monthly until dosing is stopped or adjusted further at the discretion of the treating medical professional. In some aspects, the dosing can occur no more frequently than every other day. In other words, no two doses are be separated by fewer than 48 hours in some aspects.

In some embodiments, patients may have a therapeutic regimen that omits taking a known potent inhibitor of hepatic CYP 3A activity (e.g., erythromycin, clarithromycin, ketoconazole, itraconazole, etc.) within 1 week or within a period less than 5 times the drug's half-life, whichever is longer, before administration of ketamine. Preferably, the patient waits at least a week after a lost dose of the hepatic CYP 3A activity inhibitor.

In some embodiments, patients may have a therapeutic regimen that omits use or psychostimulants or benzodiazepines within 8 hours of ketamine dosing. Benzodiazepines may be used as rescue medications in the clinic following dosing and under the direction of the treating medical professional.

In some embodiments, patients may have a therapeutic regimen that omits use of the following medications while undergoing a course of treatment with ketamine: lamotrigine, acamprosate, memantine, riluzole, or lithium.

In some embodiments, patients may experience severe nausea, anxiety, agitation, elevations in blood pressure, or psychosis from the ketamine treatment. The following rescue medications may be used if needed during the ketamine infusion to inhibit these negative side effects: Lorazepam at 1 mg IM may be given for anxiety or agitation as required; Ondansetron ODT at 4-8 mg PO every twelve hours for nausea or vomiting; Ondansetron at 4-8 mg IV for nausea or vomiting; Haloperidol at 1 mg IM or IV can be given for agitation or psychosis; Benztropine at 2 mg IM or IV may be administered for a dystonic reaction as required; and/or Labetalol at 10 mg IV over 2 minutes then 10 mg IV every 10 minutes, total dose not to exceed 300 mg.

During treatment with ketamine, the following safety monitoring can occur for the patient. Blood pressure and heart rate measurements can be assessed supine with a completely automated device. Automated monitoring of vital signs (e.g., pulse/heart rate, respiratory rate, blood pressure) can be performed during each ketamine infusion. Monitoring can start 5 minutes prior to start of infusion of ketamine and continue until 1 hour after the start of the infusion. More specifically, automated monitoring of blood pressure every 10 minutes with more frequent monitoring can occur if elevated readings are obtained. Consideration may be given to not dosing any patient with ketamine who has a pre-dose blood pressure of >150 systolic and/or 90 diastolic. Continuous pulse oximetry can be performed during each ketamine infusion, where pulse oximetry can start 5 minutes prior to start of infusion of ketamine and continue until 1 hour after the start of the infusion.

In some embodiments, ratings are used to assess level of consciousness can be completed at about every fifteen minutes, which can include the Modified Observer's Assessment of Alertness/Sedation (MOAA/S). If the patient experiences significant or lingering sedation, consideration will be given to prolonging the on-site monitoring period. A MOAA/S score of 5 indicates that the patient responds readily to name spoken in normal tone and are awake, which is minimal sedation. A MOAA/S score of 4 indicates the patient is lethargic to respond to name spoken in normal tone, which is moderate sedation. A MOAA/S score of 3 indicates the patient responds after name called loudly or repeatedly, which is moderate sedation. A MOAA/S score of 2 indicates the patient has purposeful response to mild prodding or mild shaking, which is moderate sedation. A MOAA/s score of 1 indicates the patient responds to trapezius squeeze or other painful stimulus with purposeful and reflexive withdrawal, which is deep sedation. A MOAA/S score of 0 indicates patient has no response to painful stimulus (e.g., trapezius squeeze), which can be considered being under general anesthesia.

In some embodiments, the decision to discharge the patient following dosing can be up to the treating medical professional (e.g., psychiatrist or ARNP). All patients should not drive or operate machinery until 24 hours after dosing with ketamine. At any point in the follow-up period, if a patient is deemed to pose a significant risk to themselves or others, hospitalization is immediately recommended or enforced.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. A method of treating the symptoms of symptomatic amyotrophic lateral sclerosis (ALS) in a subject, the method comprising:
   providing the subject having been diagnosed with ALS, wherein the subject is in a symptomatic stage of ALS;
   providing ketamine;
   administering the ketamine to the subject having ALS after onset of muscle wasting or deterioration of muscle function; and
   inhibiting muscle wasting or deterioration of muscle function and progression of limb paralysis in the subject having ALS with the ketamine and prolonging survival of the subject.

2. The method of claim 1, comprising administering the ketamine so that the subject has an improvement of a condition of ALS.

3. The method of claim 2, wherein the improvement in the condition of ALS includes at least one of:
   improvement in probability of prolonging survival;
   improvement in rate of deterioration of body weight;
   improvement in projected days of survival; or
   improvement in days of life after 20% loss of body weight before death.

4. The method of claim 3, comprising administering the ketamine so that the subject has an extended life expectancy.

5. The method of claim 4, wherein the extended life expectancy is determined by a higher probability of prolonging survival compared to without being administered ketamine.

6. The method of claim 4, wherein the extended life expectancy is determined by a higher probability of survival compared to another subject having ALS with a similar life expectancy that is not administered ketamine.

7. The method of claim 3, comprising administering the ketamine so that the subject has a slower rate of deterioration of body weight.

8. The method of claim 7, wherein the slower rate is compared to a rate of deterioration of body weight of the subject prior to being administered ketamine.

9. The method of claim 3, comprising administering the ketamine so that the subject has a higher number of projected days of the prolonged survival.

10. The method of claim 9, wherein the higher number of projected days of the prolonged survival are compared to a number of projected days of survival for the subject prior to being administered ketamine.

11. The method of claim 3, comprising administering the ketamine after the subject has lost 20% of body weight compared to an initial body weight so that the subject has an improvement in days of life until death.

12. The method of claim 11, wherein the improvement in days of life increases latency between 20% loss of body weight and death.

13. The method of claim 1, wherein the subject being administered ketamine has less than or about 80% body weight compared to an initial body weight.

14. The method of claim 1, wherein the ketamine is administered in dosing from about 0.1 mg/kg to about 100 mg/kg.

15. The method of claim 14, wherein the dosing is at most every other day.

16. The method of claim 14, wherein the dosing includes dosing twice weekly for a first period of time and then once weekly for a second period of time.

17. A method of treating the symptoms of symptomatic amyotrophic lateral sclerosis (ALS) to extend life expectancy in a subject, the method comprising:
providing the subject having been diagnosed with ALS, wherein the subject is in a symptomatic stage of ALS;
providing ketamine; and
administering the ketamine to the subject having ALS after onset of muscle wasting or deterioration of muscle function, wherein the ketamine is administered in order to inhibit progression of limb paralysis and to provide the subject with an extended life expectancy compared to life expectancy of the subject prior to being administered the ketamine, wherein the extended life expectancy is determined by the subject having a first progression rate of ALS prior to being administered ketamine and a second progression rate of ALS after being administered ketamine, wherein the first progression rate is faster than the second progression rate such that the progression of ALS in the subject is slowed by the ketamine.

18. The method of claim 1, further comprising monitoring the muscle function of the subject.

19. The method of claim 17, further comprising monitoring the muscle function of the subject.

20. The method of claim 17, wherein an increase in life expectancy is desirable to the subject.

* * * * *